(12) United States Patent
Yamashita et al.

(10) Patent No.: US 7,829,499 B2
(45) Date of Patent: Nov. 9, 2010

(54) GRANULAR PESTICIDE PREPARATION

(75) Inventors: Hayase Yamashita, Tokyo (JP);
Kiyotoshi Nishiyama, Tokyo (JP);
Tetsuo Ohkawa, Tokyo (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 656 days.

(21) Appl. No.: 10/573,118

(22) PCT Filed: Sep. 22, 2004

(86) PCT No.: PCT/JP2004/013777

§ 371 (c)(1), (2), (4) Date: Mar. 23, 2006

(87) PCT Pub. No.: WO2005/029957

PCT Pub. Date: Apr. 7, 2005

(65) Prior Publication Data
US 2006/0287199 A1    Dec. 21, 2006

(30) Foreign Application Priority Data
Sep. 26, 2003   (JP) .............................. 2003-336541

(51) Int. Cl.
*A01N 25/00* (2006.01)
*A01N 25/12* (2006.01)
*A61K 9/14* (2006.01)

(52) U.S. Cl. ..................... 504/116.1; 504/367; 424/489

(58) Field of Classification Search ............... 504/116.1, 504/367
See application file for complete search history.

(56) References Cited

U.S. PATENT DOCUMENTS

| | | | | |
|---|---|---|---|---|
| 4,844,734 A * | 7/1989 | Iwasaki et al. | ............... | 504/330 |
| 5,229,356 A * | 7/1993 | Tocker | ........................ | 504/214 |
| 6,087,306 A * | 7/2000 | Bell et al. | .................... | 504/367 |
| 6,458,748 B1 * | 10/2002 | Yoshimura et al. | .......... | 504/243 |
| 6,723,682 B2 * | 4/2004 | Yamada et al. | ............... | 504/132 |
| 2004/0011262 A1 | 1/2004 | Fujita et al. | | |
| 2005/0250648 A1 | 11/2005 | Ozaki et al. | | |

FOREIGN PATENT DOCUMENTS

| | | |
|---|---|---|
| JP | 41-10037 | 5/1966 |
| JP | 47-19042 | 9/1972 |
| JP | 63-35504 | 2/1988 |
| JP | 63-45201 | 2/1988 |
| JP | 2-288803 | 11/1990 |
| JP | 4-66509 | 3/1992 |
| JP | 4-273802 | 9/1992 |
| JP | 5-155715 | 6/1993 |
| JP | 6-505256 | 6/1994 |
| JP | 6-263601 | 9/1994 |
| JP | 63-22502 | 11/1994 |
| JP | 9-315903 | 12/1997 |
| JP | 10-109903 | 4/1998 |
| JP | 10-109904 | 4/1998 |
| JP | 2000-302602 | 10/2000 |
| JP | 2000-319103 | 11/2000 |
| JP | 2001-302576 | 10/2001 |
| JP | 2002-179507 | 6/2002 |
| JP | 2003-40702 | 2/2003 |
| JP | 2004-2260 | 1/2004 |
| WO | 92/12637 | 8/1992 |
| WO | 03/082008 A1 | 10/2003 |

* cited by examiner

*Primary Examiner*—Johann R Richter
*Assistant Examiner*—Kristie L Brooks
(74) *Attorney, Agent, or Firm*—Wenderoth, Lind & Ponack, L.L.P.

(57) ABSTRACT

The invention aims at providing a granular pesticide preparation which can be prepared by a simple and easy process and attain optimum controlled-release of pesticidal active ingredients and which is reduced in environmental load and in sufferings induced by pesticidal active ingredients and exerts stable drug effects. The invention relates to a granular pesticide preparation which consists of both non-disintegrating pesticide granules comprising an acid pesticidal active ingredient, a cationic surfactant, and a basic substance and causing no disintegration in water within 30 minutes and a pesticidal active ingredient and which has a particle size of 0.3 to 3 mm in diameter or of 0.6 to 3 mm in breadth and 2 to 10 mm in length and the property of falling into water after the application on water surface and disintegrating in water within 30 minutes.

4 Claims, No Drawings

GRANULAR PESTICIDE PREPARATION

TECHNICAL FIELD

The present invention relates to a granular pesticide preparation which shows efficacy for a long term and can reduce or prevent phytotoxicity and reduce environmental burden.

BACKGROUND TECHNOLOGY

Various preparation methods which could control dissolution of a pesticidal active ingredient have been heretofore studied aiming at phytotoxicity reduction and efficacy sustainability of a granular pesticide preparation containing a pesticidal active ingredient. For example, methods of blending paraffin wax, thermoplastic resin, activated carbon, foam granules or clay mineral in combination to attain sustained-releasability were proposed (See Japanese Patent Laid-Open No. 63-35504, Japanese Patent Laid-Open No. 63-45201 and Japanese Patent Laid-Open No. 2-288803).

However, such conventional methods for sustained-releasability were not necessarily effective and had such problems that the preparation procedure of a granular pesticide preparation was complicated and that release of the pesticidal composition was insufficient and most of the pesticidal active ingredient was not utilized and left intact in the pesticidal composition so that pesticidal active ingredients more than required would be released to the environment to result in causing a problem that the burden on the environment was significant.

A production method of a granular pesticide preparation comprising preparing an inner core and coating the inner core with an active ingredient different from that of the inner core has been also proposed aiming at stabilization of different active ingredients (See Japanese Patent Laid-Open No. 9-315903), but technique to control, in a single pesticide preparation, a pesticidal active ingredient for which sustained-releasability is necessary and a pesticidal active ingredient for which prompt release from the pesticide preparation is desired has not yet been established.

DISCLOSURE OF THE INVENTION

Under the circumstances, an object of the present invention is to provide a granular pesticide preparation which overcomes problems with conventional granular pesticide preparations, can be prepared by a simple and easy process and enables the most suitable controlled releasability needed for pesticidal active ingredients compounded, reduces environmental burden and phytotoxicity caused by pesticidal active ingredients, and shows stable efficacy.

The inventors have conducted intensive studies on granular pesticide preparations and, as a result, have arrived at a discovery that the above-mentioned problems can be solved by using those which comprise: non-disintegrable pesticide granules compounding an acidic pesticidal active ingredient with a cationic surfactant and a basic substance; and a pesticidal active ingredient, and further having a granule size of 0.3 to 3 mm in diameter or of 0.6 to 3 mm in breadth and 2 to 10 mm in length and having properties of settling in water rapidly after application on the water surface and disintegration in water within 30 minutes, leading to completion of the present invention on the basis of the discovery.

That is, the present invention provides:
(1) a granular pesticide preparation characterized by comprising non-disintegrable pesticide granules containing an acidic pesticidal active ingredient, a cationic surfactant and a basic substance which granules are not disintegrated in water within 30 minutes and a pesticidal active ingredient, and having a granule size of 0.3 to 3 mm in diameter or of 0.6 to 3 mm in breadth and 2 to 10 mm in length, wherein said preparation has properties of settling in water rapidly after application on water surface and of disintegration in water within 30 minutes;
(2) the granular pesticide preparation according to (1) above, wherein the acidic pesticidal active ingredient has a pKa of 2 to 7;
(3) the granular pesticide preparation according to (1) above, wherein the acidic pesticidal active ingredient is a herbicide;
(4) the granular pesticide preparation according to (3) above, wherein the herbicide is a sulfonylurea-based compound;
(5) the granular pesticide preparation according to (3) above, wherein the herbicide is a difluoromethanesulfonylanilide derivative represented by the general formula (I):

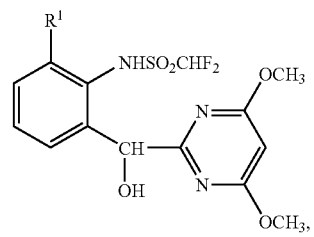

($R^1$ in the formula is a hydrogen atom, an alkyl group or an alkoxyalkyl group) or a salt thereof;
(6) the granular pesticide preparation according to (1) above, wherein the basic substance is sodium hydrogen carbonate, sodium carbonate, calcium hydroxide, calcium carbonate, basic white carbon or basic Japanese acid clay;
(7) the granular pesticide preparation according to (1) above, wherein the cationic surfactant is gelled or becomes swollen in water;
(8) a production method of a granular pesticide preparation characterized in that non-disintegrable pesticide granules and a pesticidal active ingredient are subjected to a granulating treatment together with a surfactant and an extender to form granules having a granule size of 0.3 to 3 mm in diameter or of 0.6 to 3 mm in breadth and 2 to 10 mm in length, wherein said non-disintegrable pesticide granules contain an acidic pesticidal active ingredient, a cationic surfactant and a basic substance, and are not disintegrated in water within 30 minutes;
(9) the production method according to (8) above, wherein the granulating treatment is performed by extrusion granulation through a screen of which the mesh opening has a diameter larger than the granule size or granule length of the non-disintegrable pesticide granules.

BEST MODE FOR CARRYING OUT INVENTION

The present invention is described in detail hereinbelow.

The non-disintegrable pesticide granules to be contained in the granular pesticide preparation of the present invention are those which are not disintegrated in water within 30 minutes and keep the original granular form.

The acidic pesticidal active ingredient used in the non-disintegrable pesticide granules is not particularly limited, but usually it is a herbicide, a plant growth regulator, a fungicide, an insecticide and the like of which those having a pKa in the range of 2 to 7 are preferable including geometrical isomers, optical isomers and the like.

The pesticidal active ingredient used in the granular pesticide preparation of the present invention is not particularly limited, but usually it is a herbicide, a plant growth regulator, a fungicide, an insecticide and the like of which those having a pKa in the range of 2 to 7 are preferable as an acidic pesticidal active ingredient, and geometrical isomers, optical isomers and the like are also included.

The herbicide is not particularly limited, but as an acidic pesticidal active ingredient, those having a pKa in the range of 2 to 7 are preferable of which those of a sulfonylurea-based compound and a difluoromethanesulfonylanilide derivative represented by the general formula (I):

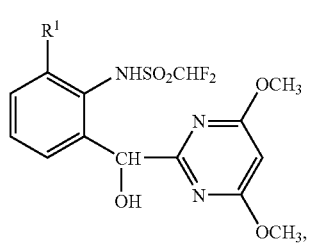

(I)

($R^1$ in the formula is a hydrogen atom, an alkyl group or an alkoxyalkyl group) or a salt thereof are particularly preferable.

Examples of the sulfonylurea-based compound include 1-(4,6-dimethoxypyrimidin-2-yl)-3-[1-methyl-4-(2-methyl-2H-tetrazol-5-yl)pyrazol-5-ylsulfonyl]urea(azimsulfuron), 1-(2-chloroimidazo[1,2-a]pyridin-3-ylsulfonyl)-3-(4,6-dimethoxypyrimidin-2-yl)urea(imazosulfuron), ethyl 5-(4,6-dimethoxypyrimidin-2-ylcarbamoylsulfamoyl)-1-methylpyrazole-4-carboxylate(pyrazosulfuron-ethyl), methyl α-(4,6-dimethyoxypyrimidin-2-ylcarbamoylsulfamoyl)-O-toluate(bensulfuron-methyl), 1-(4,6-dimethoxypyrimidin-2-yl)-3-(2-ethoxyphenoxysulfonyl)urea(ethoxysulfuron), 1-[2-(cyclopropylcarbonyl)anilinosulfonyl]-3-(4,6-dimethoxypyrimidin-2-yl)urea(cyclosulfamuron), 1-(4,6-dimethoxy-1,3,5-triazin-2-yl)-3-[2-(2-methoxyethoxy)phenylsulfonyl]urea(cinosulfuron), methyl 3-(4-methoxy-6-methyl-1,3,5-triazin-2-ylcarbamoylsulfamoyl)-2-thenoate (thifensulfuron-methyl), 2-(4,6-dimethoxypyrimidin-2-ylcarbamoylsulfamoyl)-N,N-dimethylnicotinamide (nicosulfuron), methyl 3-chloro-5-(4,6-dimethoxypyrimidin-2-ylcarbamoylsulfamoyl)-1-methylpyrazole-4-carboxylate(halosulfuron-methyl), 1-(4,6-dimethoxypyrimidin-2-yl)-3-(3-trifluoromethyl-2-pyridylsulphonyl)urea(flazasulfuron), 1-(4,6-dimethoxypyrimidin-2-yl)-3-(3-ethylsulfonyl-2-pyridylsulfonyl)urea(rimsulfuron) and the like.

Examples of the difluoromethanesulfonylanilide derivative or the salt thereof include the compounds described in Japanese Patent Laid-Open No. 2000-44546, for example, 2-[(4,6-dimethoxypyrimidin-2-yl)hydroxymethyl]-N-difluoromethanesulfonyl anilide, 2-[(4,6-dimethoxypyrimidin-2-yl)hydroxymethyl]-6-methoxymethyl-N-difluoromethanesulfonyl anilide, 2-[(4,6-dimethoxypyrimidin-2-yl)hydroxymethyl]-6-ethyl-N-difluoromethanesulfonyl anilide and the like.

Examples of other herbicides include S-ethyl 2-methyl-4-chlorophenoxythioacetate(phenothiol), α-(2-naphthoxy) propionanilide(naproanilide), methyl 5-(2,4-dichlorophenoxy)-2-nitrobenzoate(bifenox), S-4-chlrorobenzyl-N,N-diethyl thiocarbamate(benthiocarb), S-benzyl 1,2-dimethylpropyl(ethyl)thiocarbamate(esprocarb), S-ethyl hexahydro-1H-azepine-1-carbothioate(molinate), S-1-methyl-1-phenylethyl piperidine-1-carbothioate(dimepiperate), O-3-tert-butylphenyl 6-methoxy-2-pyridyl(methyl)thiocarbamate(pyributicarb), 2-chloro-2',6'-diethyl-N-(butoxymethyl)acetanilide(butachlor), 2-chloro-2',6'-diethyl-N-(2-propoxyethyl)acetanilide(pretilachlor), (RS)-2-bromo-N-(α,α-dimethylbenzyl)-3,3-dimethylbutyramide(bromobutide), 2-benzothiazol-2-yloxy-N-methylacetanilide(mefenacet), 1-(α,α-dimethylbenzyl)-3-(p-tolyl)urea(dymron), 2-methylthio-4,6-bis(ethylamino)-s-triazine(simetryn), 2-methylthio-4,6-bis(isopropylamino)-s-triazine(prometryn), 2-methylthio-4-ethylamino-6-(1,2-dimethylpropylamino)-s-triazine(dimethametryn), 2,4-dichlorophenyl-3'-methoxy-4'-nitrophenyl ether(chlomethoxynil), 5-tert-butyl-3-(2,4-dichloro-5-isopropoxyphenyl)-1,3,4-oxadiazol-2-(3H)-one (oxadiazon), 4-(2,4-dichlorobenzoyl)-1,3-dimethyl-5-pyrazolyl-p-toluenesulfonate(pyrazolate), 2-[4-(2,4-dichlorobenzoyl)-1,3-dimethylpyrazol-5-yloxy] acetophenone(pyrazoxyfen), (RS)-2-(2,4-dichloro-m-tolyloxy)propionanilide(clomeprop), 2-[4-(2,4-dichloro-m-toluoyl)-1,3-dimethylpyrazol-5-yloxy)-4'-methylacetophenone(benzofenap), S,S'-dimethyl 2-difluoromethyl-4-isobutyl-6-trifluoromethylpyridine-3,5-dicarbothioate(dithiopyl), 2-chloro-N-(3-methoxy-2-thenyl)-2',6'-dimethylacetanilide(thenylchlor), butyl(R)-2-[4-(4-cyano-2-fluorophenoxy)phenoxy]propionate(cyhalofop-butyl), 3-[1-(3,5-dichlorphenyl)-1-methylethyl]-2,3-dihydro-6-methyl-5-phenyl-4H-1,3-oxazine-4-one (oxaziclomefone), 3-(4-chloro-5-cyclopentyloxy-2-fluorophenyl)-5-isopropylidene-1,3-oxazolidin-2,4-dione (pentoxazone), 1-(diethylcarbamoyl)-3-(2,4,6-trimethylphenylsulfonyl)-1,2,4-triazole(cafenstrole), methyl 2-[(4,6-dimethoxypyrimidin-2-yl)oxy]-6-[(E)-1-(methoxyimino)ethyl]benzoate(pyriminobac-methyl) and the like.

The plant growth regulator is not particularly limited, but 4'-chloro-2'-(α-hydroxybenzyl)isonicotinanilide(inabenfide), (2RS,3RS)-1-(4-chlorophenyl)-4,4-dimethyl-2-(1H-1,2,4-triazol-1-yl)pentan-3-ol(paclobutrazol), (E)-(S)-1-(4-chlorophenyl)-4,4-dimethyl-2-(1H-1,2,4-triazol-1-yl)pent-1-en-3-ol (uniconazole), calcium 3-oxido-5-oxo-4-propionylcyclohex-3-enecarboxylate(prohexadione-calcium), maleic hydrazide choline and the like are included. Among these, those having a pKa of 2 to 7 can be particularly preferably used as the acidic pesticidal active ingredient.

The fungicide is not particularly limited, but O,O-diisopropyl-S-benzylthiophosphate (IBP), 3'-isopropoxy-2-methylbenzanilide(mepronil), α,α,α-trifluoro-3'-isopropoxy-o-toluanilide (flutolanil), 3,4,5,6-tetrachloro-N-(2,3-dichlorophenyl)phthalamic acid (tecloftalam), 1-(4-chlorobenzyl)-1-cyclopentyl-3-phenylurea(pencycuron), 6-(3,5-dichloro-4-methylphenyl)-3(2H)-pyridazinone(diclomezine), methyl N-(2-methoxyacetyl)-N-(2,6-xylyl)-DL-alaninate(metalaxyl), (E)-4-chloro-α,α,α-trifluoro-N-(1-imidazol-1-yl-2-propoxyethylidene)-o-toluidine (triflumizole), kasugamycin, validamycin, 3-allyloxy-1,2-benzoisothiazole-1,1-dioxide(probenazole), diisopropyl 1,3-dithiolan-2-ylidenemalonate(isoprothiolane), 5-methyl-1,2,4-triazolo[3,4-b]benzothiazole(tricyclazole), 1,2,5,6-tetrahydropyrrolo[3,2,1-ij]quinolin-4-one (pyroquilon), 5-ethyl-5,8-dihydro-8-oxo[1,3]dioxolo[4,5-g]quinoline-7-carboxylic acid (oxolinic acid), (Z)-2'-methylacetophenone 4,6-dimethylpyrimidin-2-ylhydrazone-4,5,6,7-tetrachloro phthalide(ferimzone), 3-(3,5-dichlorophenyl)-N-isopropyl- 2,4-dioxoimidazolidine-1-carboxamide(iprodione) and the like are included. Among these, those having a pKa of 2 to 7 can be particularly preferably used as the acidic pesticidal active ingredient.

The insecticide is not particularly limited, but O,O-dimethyl-O-(3-methyl-4-nitrophenyl)thiophosphate (MEP), (2-isopropyl-4-methylpyrimidyl-6-)-diethylthiophosphate (diazinon), 1-naphthyl-N-methyl carbamate (NAC), O,O-diethyl-O-(3-oxo-2-phenyl-2H-pyridazin-6-yl)phosphorothioate (pyridafenth ion), O,O-dimethyl-O-3,5,6-trichloro-2-pyridylphosphorothioate(chlorpyrifos-methyl), dimethyidicarbethoxyethyldithiophosphate(marathion), O,O-dimethyl-S—(N-methylcarbamoylmethyl)dithiophosphate(dimethoate), O,O-dipropyl-O-4-methylthiophenylphosphate(propaphos), O,S-dimethyl-N-acetylphosphoramidothioate(acephate), ethyl p-nitrophenylthionobenzene phosphonate (EPN), 2-sec-butylphenyl-N-methylcarbamate (BPMC), 2,3-dihydro-2,2-dimethyl-7-benzo[b]furanyl N-dibutylaminothio-N-methylcarbamate(carbosulfan), ethyl N-[2,3-dihydro-2,2-dimethylbenzofuran-7-yloxycarbonyl(methyl)aminothio]-N-isopropyl-β-alaninate (benfuracarb), (RS)-α-cyano-3-phenoxybenzyl (RS)-2,2-dichloro-1-(4-ethoxyphen-yl)cyclopropanecarboxylate(cycloprothrin), 2-(4-ethoxyphenyl)-2-methylpropyl 3-phenoxybenzyl ether (etofenprox), 1,3-bis(carbamoylthio)-2-(N,N-dimethylamino)propane hydrochloride(cartap), 5-dimethylamino-1,2,3-trithiane oxalate (thiocyclam), S,S'-2-dimethylaminotrimethylene di(benzenethiosulfonate) (bensultap), 2-tert-butylimino-3-isopropyl-5-phenyl-1,3,5,6-tetrahydro-2H-1,3,5-thiadiazine-4-one (buprofezin) and the like are included. Among these, those having a pKa of 2 to 7 can be particularly preferably used as the acidic pesticidal active ingredient.

When the acidic pesticidal active ingredient having the above specified pKa is used, the pKa of the ingredient is, for example, measured by a method described in "Jikken Kagaku Kouza", Vol. 5 (thermal measurement and equilibrium), p. 469-p. 474, Maruzen Co., Ltd. published Jan. 20, 1958 and elsewhere.

The cationic surfactant used in the present invention is not particularly limited, but preferably includes amine salt ones, pyridinium salt ones, quaternary ammonium salt ones and the like.

Examples of the amine salt cationic surfactant include laurylamine hydrochloride, stearylamine hydrochloride, oleylamine acetate, stearylamine acetate, stearyl aminopropylamine acetate and the like.

Examples of the pyridinium salt cationic surfactant include laurylpyridinium chloride, myristylpyridinium chloride, cetylpyridinium chloride and the like.

Examples of the quaternary ammonium salt cationic surfactant include alkyldimethylbenzyl ammonium chloride, lauryltrimethylammonium chloride, cetyltrimethylammonium chloride, stearyltrimethylammonium chloride, dilauryldimethylammonium chloride, dioleoyldimethylammonium chloride, dicocoyldimethylammonium chloride, distearyldimethylammonium chloride, lauryldihydroxyethylmethyl ammonium chloride, oleylbispolyoxyethylenemethylammonium chloride, stearylhydroxyethyldimethylammonium chloride, lauryidimethylbenzylammonium chloride, lauroylaminopropyldimethylethylammonium ethosulfate, lauroylaminopropyldimethylhydroxyethylammonium perchlorate and the like.

Particularly preferred as the cationic surfactant showing gelation or swelling in water, for example, dialkyldimethylammonium chloride wherein the alkyl part has 8-22 carbon atoms, and, above all dilauryidimethylammonium chloride, dioleyldimethylammonium chloride, dicocoyldimethylammonium chloride, distearyldimethylammonium chloride and the like. These surfactants can be used singly or can be used as a combination of two kinds or more.

The basic substance used in the present invention is not particularly limited, but those having a pH of 7.5 or higher, above all, at pH of 9 to 12 in a 1 mass % aqueous solution or a 1 mass % aqueous suspension are preferable. Examples of such a substance include hydroxides of alkaline metals and alkali earth metals, alkali metal salts and alkaline earth metal salts, compounds or minerals including the same, and others. More specific examples thereof include sodium hydroxide, potassium hydroxide, sodium hydrogen carbonate, sodium carbonate, calcium hydroxide, calcium carbonate, calcium oxide, basic white carbon, basic Japanese acid clay and the like, of which sodium hydrogen carbonate, sodium carbonate, calcium hydroxide, calcium carbonate, basic white carbon and basic Japanese acid clay are particularly preferable. These basic substances can be used singly or can be used as a combination of two kinds or more.

It is optional according to need that the granular pesticide preparation of the present invention contains additional ingredients which are usually used for a pesticide preparation. These additional ingredients to be used include a surfactant, an extender, auxiliary ingredients and the like.

The surfactant is not particularly limited, and exemplified, for example, by nonionic surfactants such as polyoxyalkyleneglycol higher fatty acid esters, polyoxyalkylene alkyl ethers, polyoxyalkylene alkylaryl ethers, polyoxyalkylene alkylaryl phenyl ethers, sorbitan monoalkylates, acetyleneglycol, polyoxyethylene-acetyleneglycol and the like, alkylaryl sulfonate, dialkyl sulfonate, alkyl sulfate ester salts, alkylphosphate ester salts, alkyl aryl phosphate, alkyl aryl phosphate ester salts, polyoxyalkylene alkyl ether sulfate ester salts, naphthalenesulfonate and condensates thereof, alkyl naphthalenesulfonate and condensates thereof, lignosulfonate, polycarboxylic acid-based polymer surfactants such as acrylic acid-itaconic acid copolymers, methacrylic acid-itaconic acid copolymers, maleic acid-styrene copolymers and maleic acid-isobutylene copolymers as well as alkali metal salts thereof, anionic surfactants such as polyoxyalkylene arylphenyl ether sulfate ester salts, and so on. These can be used singly or can be used as a combination of two kinds or more.

As the extender, solid carriers such as mineral carriers and the like, water-soluble salts and the like are used, and specific examples thereof include clays, calcium carbonate, bentonite, talc, diatomaceous earth, Japanese acid clay, silica sand, granular calcium carbonate, granular diatomaceous earth, granular Japanese acid clay, calcium stearate, white carbon, potassium chloride, anhydrous sodium sulfate, potassium sulfate, urea, ammonium sulfate, sodium benzoate and the like. These can be used singly or can be used as a combination of two kinds or more.

The auxiliary ingredients are exemplified by a binder used for preparing a granular composition including, specifically, sodium carboxymetyl cellulose, dextrin, water-solubility starch, xanthan gum, guar gum, sucrose, poly(vinylpyrrolidone), poly(vinyl alcohol), sodium polyacrylate, poly(ethylene glycol) having an average molecular weight of 6000 to 20000, poly(ethylene oxide) having an average molecular weight of 100000 to 5000000 and the like. The organic solvent which is used for dissolving the acidic pesticidal active ingredient and the cationic surfactant and allowing them to be adsorbed on a carrier includes, specifically, alkylnaphthalene, dimethyl formamide, dimethyl sulfoxide, N-methyl-2-pyrrolidinone, N-octylpyrrolidone, polyhydric alcohols, silicone oils, and the like. In addition, a disintegrator, a stabilizing agent, a plant fragment and the like can also be used according to need. These can be used singly or can be used as a combination of two kinds or more.

The composition of the non-disintegrable pesticide granules in a granular pesticide preparation of the present invention is usually selected in the range of 0.1 to 30 mass % for the acidic pesticidal active ingredient, 1 to 30 mass % for the cationic surfactant and 0.5 to 95 mass % for the basic substance, and preferably adjusted so that a 1 mass % aqueous suspension of the non-disintegrable pesticide granules usually has a pH of 5 or higher or, preferably, 7 or higher or, more preferably, 7.5 to 11.5.

The composition of the granular pesticide preparation of the present invention is usually selected in the range of 5 to 90 mass % for the non-disintegrable pesticide granules, 0.1 to 30 mass % for the pesticidal active ingredient, 0 to 20 mass % or, preferably, 0.5 to 15 mass % for the surfactant, 0 to 95 mass % or, preferably, 5 to 80 mass % for the extender, 0 to 50 mass % or, preferably, 0.5 to 40 mass % for the auxiliary ingredients, and more preferably selected in such a range that each granule has a specific gravity of 1 or more and was settled in water promptly or, preferably, within 20 minutes.

When the granular pesticide preparation of the present invention, after applied in a farm field, is settled in water and is disintegrated within 30 minutes, the pesticidal active ingredient therein dissolves, while non-disintegrable pesticide granules contained in the pesticide preparation disperse to the surface of the soil. The pesticide granules are disintegrated afterwards and the acidic pesticidal active ingredient contained therein dissolves. That is, the granular pesticide preparation of the present invention is a sustained-release pesticide preparation allowing dissolution of the pesticidal active ingredients to be sustained-release.

In the granular pesticide preparation of the present invention, dissolution characteristics suitable for pesticidal active ingredients compounded therein can be designed by combining two or more kinds of non-disintegrable pesticide granules and having them contained in the granular pesticide preparation.

In addition, the present invention encompasses a mixed pesticide preparation in which this granular pesticide preparation and another granular pesticide preparation containing neither a cationic surfactant nor a basic substance are mixed in a mass ratio of 1:9 to 9:1.

The granular pesticide preparation of the present invention has itself a size, typically, of 0.3 to 3 mm in diameter or, preferably, 0.5 to 2 mm if it is spherical, and typically of 0.6 to 3 mm or, preferably, 0.8 to 1.5 mm in breadth, and 2 to 10 mm or, preferably, 2.5 to 8 mm in length if it is elongated, while non-disintegrable pesticide granules contained in this pesticide preparation has a size typically of 0.01 to 2 mm in diameter or, preferably, 0.05 to 1 mm if it is spherical, and typically of 0.1 to 1.5 mm or, preferably, 0.3 to 1 mm in breadth, and 0.6 to 5 mm or, preferably, 1 to 3 mm in length if it is elongated.

A method for preparing the granular pesticide preparation of the present invention and non-disintegrable pesticide granules contained in the preparation is not particularly limited and, for example, heretofore known methods such as rolling granulation, extrusion granulation, coating granulation and the like are used.

The preferable production method of the granular pesticide preparation of the present invention includes a method in which non-disintegrable pesticide granules containing an acidic pesticidal active ingredient, a cationic surfactant and a basic substance which are not disintegrated in water within 30 minutes and a pesticidal active ingredient are subjected to a granulating treatment together with a surfactant and an extender to form granules having a granule size of 0.3 to 3 mm in diameter or of 0.6 to 3 mm in breadth and 2 to 10 mm in length.

(Production of Non-Disintegrable Pesticide Granules)

The rolling granulation method comprises a step of putting an acidic pesticidal active ingredient, a cationic surfactant and a basic substance together with auxiliary ingredients such as a binder, an extender and the like in a rolling granulation apparatus to prepare a particulate raw material, a step of gradually adding an appropriate amount of water or an aqueous solution which has dissolved a binder to this particulate raw material to prepare a granular composition having a granule size or granule length to be aimed at and a step of coating this granular composition with a film forming substance on the surface according to need, and screening after drying.

The extrusion granulation method comprises a step of subjecting an acidic pesticidal active ingredient, a cationic surfactant and a basic substance together with an auxiliary ingredients such as a binder, an extender and the like to air mill grinding or mechanochemical grinding to prepare a particulate raw material, a step of kneading a mixture obtained by adding an appropriate amount of water to this particulate raw material with a kneader such as a two-screw kneader, an extrusion granulation apparatus and the like and then granulating by extrusion through a screen of which the mesh opening diameter is set so that they have a granule size or granule length to be aimed to prepare a granular composition and a step of coating this granular composition with a film forming substance on the surface according to need, and screening after drying.

The coating granulation method comprises a step of air milling or mechanochemically grinding an acidic pesticidal active ingredient and a basic substance optionally with a cationic surfactant and auxiliary ingredients such as an extender and the like to prepare a particulate raw material, a step of putting an oil absorbing granular substance having a predetermined granule size or granule length into a conical screw mixer, mixing a cationic surfactant diluted with a solvent and optional auxiliary ingredients such as a binder and the like by simultaneous spraying, and coating the resultant oil absorbing granular substance with the particulate raw material obtained at the preceding step to prepare a granular composition and a step of screening the granular composition after optionally drying.

(Production of Granular Pesticide Preparation)

The extrusion granulation method comprises a step of adding the non-disintegrable pesticide granules obtained by the above-mentioned production method, an acidic pesticidal active ingredient and other pesticidal active ingredients together with a surfactant, an extender and optional auxiliary ingredients such as a binder, a stabilizing agent and the like followed by kneading by using a kneader such as a two-screw kneader, an extrusion granulator and the like with an appropriate amount of water, and then granulating the thus obtained mixture by extrusion through a screen of which the mesh opening has a diameter larger than the granule size or granule length of the non-disintegrable pesticide granules to prepare a granular composition and a step of coating this granular composition with a film forming substance on the surface according to need, and screening the same after drying.

The rolling granulation method comprises a step of putting the non-disintegrable pesticide granules obtained by the above-mentioned production method, an acidic pesticidal active ingredient and other pesticidal active ingredients together with auxiliary ingredients such as a surfactant, an extender and a binder and a stabilizing agent used according to need in a rolling granulation apparatus to prepare a particulate raw material, a step of gradually adding an appropriate amount of water or an aqueous solution which has dissolved a binder to this particulate raw material to prepare a granular composition having a granule size or granule length to be aimed at and a step of coating same with a film forming substance according to need, and screening after drying.

In these production methods, drying treatment can be preferably performed with a suitable drying device such as a fluidized-bed drier, a vacuum drying device and the like.

In the granular pesticide preparation of the present invention, an acidic pesticidal active ingredient having a pKa of 2 to 7, inter alia, a herbicide such as, for example, a herbicide comprising a sulfonylurea-based compound or, particularly, a difluoromethanesulfonylanilide derivative represented by the above-given general formula (I) or a salt thereof and a cationic surfactant which is gelled or becomes swollen in water are preferably used.

In the following, the present invention is described in detail by way of Examples and Test Examples, but the present invention is not limited to these Examples at all. Term of parts in each Example refers to parts by mass.

The pesticidal active ingredients used in respective Examples each had a pKa of 2 to 7, and the basic substances had a pH of 7.5 or higher in a 1 mass % aqueous solution or a 1 mass % aqueous suspension, and the non-disintegrable pesticide granules had a pH of 5 or higher in a 1 mass % aqueous suspension.

In addition, each of the cationic surfactant used in any of Examples 1 to 6 gelated in water.

Furthermore, the granular pesticide preparations obtained in each Example were settled in rapidly after putting into water and were disintegrated within 30 minutes after application and dispersed the non-disintegrable pesticide granules and the pesticidal active ingredients on the surface of the soil.

Example 1

A mixture obtained by uniformly mixing 2.55 parts of bensulfuronmethyl (pKa 5.03), 5 parts of distearyldimethylammonium chloride, 2 parts of basic white carbon, 84.45 parts of calcium carbonate, 2 parts of poly(vinyl alcohol) and 4 parts of α-starch was ground in an impact grinder. The thus obtained powder was mixed and kneaded with an appropriate amount of water with a high-speed stirrer and granulated by extrusion through a screen having a mesh opening diameter of 0.3 mm in a dome-type granulator and the granules were allowed to stand at 70° C. followed by drying to obtain pesticide granules having a diameter of 0.2 to 0.4 mm and a length of 0.5 to 1.2 mm and containing 2.55 mass % of bensulfuron-methyl. The thus obtained pesticide granules were put into water and observation was made for disintegration of the granules after 30 minutes to find no disintegrated granules so that they were concluded to be non-disintegrable.

Then, 85 parts of mefenacet and 15 parts of white carbon were uniformly mixed and finely ground by an air mill to prepare a mefenacet-containing powder. A mixture obtained by adding, in an appropriate amount of water, 11.77 parts of this mefenacet-containing powder, 20 parts of the non-disintegrable pesticide granules mentioned above, 0.5 part of sodium dodecylbenzenesulfonate, 2 parts of polyoxyethylene styrylphenyl ether ammonium sulfate, 2 parts of an enzymatically modified dextrin, 2 parts of sodium tripolyphosphate, 20 parts of bentonite and 41.73 parts of calcium carbonate were kneaded with a 2-screw kneader and granulated by extrusion through a screen having a mesh opening diameter of 1.5 mm using an extrusion granulator to attain the target size, dried by a fluidized-bed drier with the product temperature of 70° C. and screened, and thereby a granular pesticide preparation containing 0.51 mass % of bensulfuron-methyl and 10 mass % of mefenacet and having a diameter of 1.4 to 1.6 mm and a length of 3 to 9 mm was obtained. The granular pesticide preparation was put in a Petri dish containing water and observed, and as a result, the preparation was rapidly settled in after putting into water, and particles of the preparation were disintegrated on the bottom of the Petri dish within 30 minutes, and the non-disintegrable pesticide granules contained in the preparation dispersed without disintegration.

Example 2

85 Parts of a compound in which $R^1$ in the general formula (I) is a methoxymethyl group (hereinafter referred to as compound A; pKa 5.75) and 15 parts of basic white carbon were uniformly mixed, and finely ground by an air mill to prepare a compound A-containing powder.

While 76.11 parts of granular diatomaceous earth having a particle size of 42 to 60 mesh (250 to 355 μm) was introduced into a conical screw mixer and stirred, a cationic surfactant solution separately prepared beforehand by mixing and dissolving 10 parts of dioleoyldimethylammonium chloride, 6 parts of propylene glycol and 2 parts of poly(propylene glycol) (molecular weight: 1000) was introduced put thereinto under stirring. Rapidly after the introduction was completed, 5.89 parts of the above compound A-containing powder was put in and uniformly mixed to form granules and the granules were subjected to aging in a shelf drier at 70° C. to obtain pesticide granules containing 5.0 mass % of the compound A and having a particle size of 0.25 to 0.36 mm in diameter. The pesticide granules were put into water and observation was made for disintegration of the granules after 30 minutes to find no disintegrated granules and they were concluded to be non-disintegrable.

Then, a mixture obtained by adding, in an appropriate amount of water, 10 parts of the non-disintegrable pesticide granules, 3 parts of fentrazamide finely ground by an air mill, 0.5 part of sodium dodecylbenzenesulfonate, 2 parts of polyoxyethylene styrylphenyl ether ammonium sulfate, 0.5 part of sodium salt of maleic acid-styrene-methacrylic acid copolymer, 2 parts of an enzymatically modified dextrin, 2 parts of sodium tripolyphosphate, 20 parts of bentonite and 60 parts of calcium carbonate was kneaded in a 2-screw kneader and granulated by extrusion through a screen having a mesh opening diameter of 0.8 mm using an extrusion granulator to attain the target size, dried by a fluidized-bed drier at the product temperature of 70° C. and screened to obtain a granular pesticide preparation containing 0.5 mass % of the compound A and 3 mass % of fentrazamide and having a diameter of 0.7 to 0.9 mm and a length of 2 to 6 mm. The granular pesticide preparation was put in a Petri dish containing water and observed, and as a result, the preparation was rapidly settled in after putting into water, and particles of the preparation were disintegrated on the bottom of the Petri dish within 30 minutes, and the non-disintegrable pesticide granules contained in the preparation dispersed without disintegration.

Example 3

85 Parts of the compound A (pKa 5.75) and 15 parts of basic white carbon were uniformly mixed, and finely ground by an air mill to prepare a compound A-containing powder.

While 79.11 parts of Japanese acid clay having a particle size of 24 to 48 mesh (300 to 710 μm) were introduced into a conical screw mixer and a cationic surfactant solution separately prepared beforehand by mixing and dissolving 10 parts of dioleoyldimethylammonium chloride, 4 parts of propylene glycol and 1 part of polypropylene glycol (molecular weight: 1000) was introduced thereinto under stirring. Rapidly after the introduction was completed, 5.89 parts of the above-mentioned compound A-containing powder was put in and uniformly mixed to form granules and the granules were subjected to aging in a shelf drier at 70° C. to obtain pesticide granules containing 5.0 mass % of the compound A and having a particle size of 0.3 to 0.71 mm in diameter. The pesticide granules were put into water and observation was made for disintegration of the granules after 30 minutes to find no disintegrated granules so that they were concluded to be non-disintegrable.

Then, a mixture obtained by adding, in an appropriate amount of water, 10 parts of the non-disintegrable pesticide granules, 2 parts of pentoxazone finely ground by an air mill, 0.5 part of sodium dodecylbenzenesulfonate, 2 parts of polyoxyethylene styrylphenyl ether ammonium sulfate, 0.5 part of sodium salt of maleic acid-styrene-methacrylic acid copolymer, 2 parts of an enzymatically modified dextrin, 2 parts of sodium tripolyphosphate, 20 parts of bentonite and 61 parts of calcium carbonate was kneaded in a 2-screw kneader and granulated by extrusion through a screen having a mesh opening diameter of 1.2 mm using an extrusion granulator to attain the target size, dried by a fluidized-bed drier at the product temperature of 70° C. and screened to obtain a granular pesticide preparation containing 0.5 mass % of the compound A and 2 mass % of pentoxazone and having a diameter of 1.1 to 1.3 mm and a length of 3 to 8 mm. The granular pesticide preparation was put in a Petri dish containing water and observed, and as a result, the preparation was rapidly settled in after putting into water, and particles of the preparation were disintegrated on the bottom of the Petri dish within 30 minutes, and the non-disintegrable pesticide granules contained in the preparation were dispersed without disintegration.

Example 4

2 Parts of the compound A (pKa 5.75), 3 parts of dioleoyldimethylammonium chloride and 4 parts of N-methyl-2-pyrrolidone were dissolved under heating to prepare a compound A-containing solution.

This compound A-containing solution was introduced in a conical screw mixer while mixing with 89 parts of quartz sand natural pumice bases having a particle size of 42 to 60 mesh (250 to 355 μm). After the introduction was completed, 2 parts of basic white carbon were further put in and uniformly mixed to form granules, and thereby pesticide granules containing 2.0 mass % of the compound A and having a particle size of 0.25 to 0.36 mm in diameter were obtained. The pesticide granules were put into water and observation was made for disintegration of the granules after 30 minutes to find no disintegrated granules so that they were concluded to be non-disintegrable.

Then, a mixture obtained by adding, in an appropriate amount of water, 25 parts of the non-disintegrable pesticide granules, 2 parts of cafenstrole finely ground by an air mill, 0.5 part of sodium dodecylbenzenesulfonate, 2 parts of polyoxyethylene styrylphenyl ether ammonium sulfate, 0.5 part of sodium salt of maleic acid-styrene-methacrylic acid copolymer, 2 parts of an enzymatically modified dextrin, 2 parts of sodium tripolyphosphate, 20 parts of bentonite and 46 parts of calcium carbonate was kneaded in a 2-screw kneader and granulated by extrusion through a screen having a mesh opening diameter of 1.2 mm using an extrusion granulator to attain the target size, dried by a fluidized-bed drier at the product temperature of 50° C. and screened to obtain a granular pesticide preparation containing 0.5 mass % of compound A and 2 mass % of cafenstrole and having a diameter of 1.1 to 1.3 mm and a length of 3 to 8 mm. The granular pesticide preparation was put in a Petri dish containing water and observed, and as a result, the preparation was rapidly settled in after putting into water, and particles of the preparation were disintegrated on the bottom of the Petri dish within 30 minutes, and the non-disintergrable pesticide granules contained in the preparation dispersed without disintegration.

Example 5

85 Parts of a compound in which $R^1$ in the general formula (I) was an ethyl group (hereinafter referred to as compound B; pKa 6.17) and 15 parts of basic white carbon were uniformly mixed, and finely ground by an air mill to prepare a compound B-containing powder.

While 76.11 parts of granular diatomaceous earth having a particle size of 42 to 60 mesh (250 to 355 μm) were introduced into a conical screw mixer and a cationic surfactant solution separately prepared beforehand by mixing and dissolving 10 parts of distearyldimethylammonium chloride, 6 parts of propylene glycol and 2 parts of poly(propylene glycol) (molecular weight: 1000) was introduced thereinto under stirring. Rapidly after the introduction was completed, 5.89 parts of the compound B-containing powder mentioned above was put in and uniformly mixed to form granules and the granules were subjected to aging in a shelf drier at 70° C. to obtain pesticide granules containing 5.0 mass % of the compound B and having a particle size of 0.25 to 0.36 mm in diameter. The pesticide granules were put into water and observation was made for disintegration of the granules after 30 minutes to find no disintegrated granules so that they were concluded to be non-disintegrable.

Then, a mixture obtained by adding, in an appropriate amount of water, 10 parts of the non-disintegrable pesticide granules, 0.6 part of pyriminobacmethyl finely ground by an air mill, 1.5 parts of pentoxazone finely ground by an air mill, 0.5 part of sodium dodecylbenzenesulfonate, 2 parts of polyoxyethylene styrylphenyl ether ammonium sulfate, 0.5 part of sodium salt of maleic acid-styrene-methacrylic acid copolymer, 2 parts of an enzymatically modified dextrin, 2 parts of sodium tripolyphosphate, 20 parts of bentonite and 60.9 parts of calcium carbonate was kneaded in a 2-screw kneader and granulated by extrusion through a screen having a mesh opening diameter of 1.2 mm using an extrusion granulator to attain the target size, dried by a fluidized-bed drier at the product temperature of 70° C. and screened to obtain a granular pesticide preparation containing 0.5 mass % of the compound B, 0.6 mass % of pyriminobac-methyl and 1.5 mass % of pentoxazone and having a diameter of 1.1 to 1.3 mm and a length of 3 to 8 mm. The granular pesticide preparation was put in a Petri dish containing water and observed, and as a result, the preparation was rapidly settled in after putting into water, and particles of the preparation were disintegrated on the bottom of the Petri dish within 30 minutes, and the non-disintegrable pesticide granules contained in the preparation were dispersed without disintegration.

Example 6

A mixture obtained by uniformly adding 12.5 parts of tricyclazole (pKa 1.6), 4 parts of distearyldimethylammonium chloride, 5 parts of calcium carbonate, 2 parts of poly (vinyl alcohol), 2 parts of α-starch and 73.5 parts of clay was ground in an impact grinder. The thus obtained powder was mixed with an appropriate amount of water and 2 parts of an acrylic emulsion containing 50% solid with a high-speed stirrer and granulated by extrusion through a screen having a mesh opening diameter of 0.3 mm in a dome-type granulator to attain the target size, which were then allowed to stand at 70° C. and thereby dried to obtain pesticide granules having a diameter of 0.2 to 0.4 mm and a length of 0.5 to 1.2 mm and containing 12.5 mass % of tricyclazole. The thus obtained pesticide granules were put into water and observation was made for disintegration of the granules after 30 minutes to find no disintegrated granules so that they were concluded to be non-disintegrable.

Then, a mixture obtained by adding, in an appropriate amount of water, 32 parts of the non-disintegrable pesticide granules, 2 parts of imidacloprid finely ground by an air mill, 0.5 part of sodium dodecylbenzenesulfonate, 3 parts of poly (vinyl alcohol), 20 parts of bentonite and 42.5 parts of clay was kneaded in a 2-screw kneader and granulated by extrusion through a screen having a mesh opening diameter of 1.5 mm using an extrusion granulator to attain the target size, dried by a fluidized-bed drier at the product temperature of 70° C. and screened to obtain a granular pesticide preparation containing 4 mass % of tricyclazole and 2 mass % of imidacloprid and having a diameter of 1.4 to 1.6 mm and a length of 3 to 9 mm. The granular pesticide preparation was put in a Petri dish containing water and observed, and as a result, the preparation was rapidly settled in after putting into water, particles of the preparation were disintegrated on the bottom of the Petri dish within 30 minutes, and the non-disintegrable pesticide granules contained in the preparation dispersed without disintegration.

Comparative Example 1

A mixture obtained by uniformly adding 2.55 parts of bensulfuronmethyl (pKa 5.03), 2 parts of basic white carbon, 89.45 parts of calcium carbonate, 2 parts of poly(vinyl alcohol) and 4 parts of α-starch was ground in an impact grinder. The thus obtained powder was mixed with an appropriate amount of water with a high-speed stirrer and granulated by extrusion through a screen having a mesh opening diameter of 0.3 mm in a dome-type granulator and the granules were allowed to stand at 70° C. and thereby dried to obtain pesticide granules having a diameter of 0.2 to 0.4 mm and a length of 0.5 to 1.2 mm and containing 2.55 mass % of bensulfuronmethyl. The thus obtained pesticide granules were put into water and observation was made for disintegration of the granules after 30 minutes to find no disintegrated granules so that they were concluded to be non-disintegrable.

Then, 85 parts of mefenacet and 15 parts of white carbon were uniformly mixed and finely ground by an air mill to prepare a mefenacet-containing powder. A mixture obtained by adding, in an appropriate amount of water, 11.77 parts of this mefenacet-containing powder, 20 parts of the non-disintegrable pesticide granules mentioned above, 0.5 part of sodium dodecylbenzenesulfonate, 2 parts of polyoxyethylene styrylphenyl ether ammonium sulfate, 2 parts of an enzymatically modified dextrin, 2 parts of sodium tripolyphosphate, 20 parts of bentonite and 41.73 parts of calcium carbonate was kneaded in a 2-screw kneader and granulated by extrusion through a screen having a mesh opening diameter of 1.5 mm using an extrusion granulator to attain the target size, dried by a fluidized-bed drier at the product temperature of 70° C. and screened to obtain a granular pesticide preparation containing 0.51 mass % of bensulfuron-methyl and 10 mass % of mefenacet and having a diameter of 1.4 to 1.6 mm and a length of 3 to 9 mm. The granular pesticide preparation was put in a Petri dish containing water and observed, and as a result, the preparation was rapidly settled in after putting into water, particles of the preparation were disintegrated on the bottom of the Petri dish within 30 minutes, and the non-disintegrable pesticide granules contained in the preparation dispersed without disintegration.

Comparative Example 2

A mixture obtained by uniformly mixing 0.56 part of the compound A (pKa 5.75), 2 parts of basic white carbon, 91.94 parts of calcium carbonate, 0.5 part of sodium dodecylbenzenesulfonate, 2 parts of poly(vinyl alcohol) and 2 parts of α-starch was ground in an impact grinder. The thus obtained powder was mixed with 2 parts of acrylic emulsion containing 50% solid content and an appropriate amount of water with a high-speed stirrer and granulated by extrusion through a screen having a mesh opening diameter of 0.8 mm in a dome-type granulator and the granules were allowed to stand at 70° C. and thereby dried to obtain pesticide granules having a diameter of 0.7 to 0.9 mm and a length of 2 to 6 mm and containing 0.56 mass % of the compound A. The thus obtained pesticide granules were put into water and observation was made for disintegration of the granules after 30 minutes to find no disintegrated granules so that they were concluded to be non-disintegrable.

Then, while 90 parts of the non-disintegrable pesticide granules were introduced into a conical screw mixer, 6 parts of polyoxyethylene styrylphenyl ether ammonium sulfate were introduced thereinto under stirring. After the introduction was completed, 3 parts of fentrazamide finely ground by an air mill and 1 part of white carbon were successively put in and mixed to form uniformly coated granules, and thereby a granular pesticide preparation containing 0.5 mass % of the compound A and 3 mass % of fentrazamide and having a diameter of 0.7 to 1.0 mm and a length of 2 to 7 mm was obtained. The granular pesticide preparation was put in a Petri dish containing water and observed, and as a result, the particles of the preparation was rapidly settled in after putting into water, and only a part of the preparation surface were disintegrated on the bottom of the Petri dish within 30 minutes, and the non-disintegrable pesticide granules contained in the preparation were not disintegrated.

Comparative Example 3

85 Parts of the compound B (pKa 6.17) and 15 parts of basic white carbon were uniformly mixed, and finely ground by an air mill to prepare a compound B-containing powder.

While 76.11 parts of granular diatomaceous earth having a particle size of 42 to 60 mesh (250 to 355 μm) were introduced into a conical screw mixer, 12 parts of propylene glycol and 6 parts of poly(propylene glycol) (molecular weight: 1000) were separately introduced thereinto under stirring. Rapidly after the introduction was completed, 5.89 parts of the compound B-containing powder mentioned above were put in and uniformly mixed to form granules and the granules were subjected to aging in a shelf drier at 70° C. to obtain pesticide granules having a particle size of 0.25 to 0.36 mm in diameter. The pesticide granules were put into water and observation was made for disintegration of the granules after 30 minutes to find no disintegrated granules so that they were concluded to be non-disintegrable.

Then, a mixture obtained by adding, in an appropriate amount of water, 10 parts of the non-disintegrable pesticide granules, 0.6 part of pyriminobac-methyl finely ground by an air mill, 1.5 parts of pentoxazone finely ground by an air mill, 0.5 part of sodium dodecylbenzenesulfonate, 2 parts of polyoxyethylene styrylphenyl ether ammonium sulfate, 0.5 part of sodium salt of maleic acid-styrene-methacrylic acid copolymer, 2 parts of an enzymatically modified dextrin, 2 parts of sodium tripolyphosphate, 20 parts of bentonite and 60.9 parts of calcium carbonate was kneaded in a 2-screw kneader and granulated by extrusion through a screen having a mesh opening diameter of 1.2 mm using an extrusion granulator to attain the target size, dried by a fluidized-bed drier at the product temperature of 70° C. and screened to obtain a granular pesticide preparation containing 0.5 mass % of the compound B, 0.6 mass % of pyriminobac-methyl and 1.5 mass % of pentoxazone and having a diameter of 1.1 to 1.3 mm and a length of 3 to 8 mm. The granular pesticide preparation was put in a Petri dish containing water and observed, and as a result, the preparation was rapidly settled in after putting into water, particles of the preparation were disintegrated on the bottom of the Petri dish within 30 minutes, and the non-disintegrable pesticide granules contained in the preparation dispersed without disintegration.

Comparative Example 4

A mixture obtained by uniformly mixing 12.5 parts of tricyclazole (pKa 1.6), 2 parts of poly(vinyl alcohol), 2 parts of α-starch and 82.5 parts of clay was ground in an impact grinder. The thus obtained powder was mixed with an appropriate amount of water and 2 parts of an acrylic emulsion containing 50% solid content with a high-speed stirrer and granulated by extrusion through a screen having a mesh opening diameter of 0.3 mm in a dome-type granulator and the granules were allowed to stand at 70° C. and thereby dried to obtain pesticide granules having a diameter of 0.2 to 0.4 mm and a length of 0.5 to 1.2 mm and containing 12.5 mass % of tricyclazole. The thus obtained pesticide granules were put into water and observation was made for disintegration of the granules after 30 minutes to find no disintegrated granules so that they were concluded to be non-disintegrable.

Then, a mixture obtained by adding, in an appropriate amount of water, 32 parts of the non-disintegrable pesticide granules, 2 parts of imidacloprid finely ground by an air mill, 0.5 part of sodium dodecylbenzenesulfonate, 3 parts of poly (vinyl alcohol), 20 parts of bentonite and 42.5 parts of clay was kneaded in a 2-screw kneader and granulated by extrusion through a screen having a mesh opening diameter of 1.5 mm using an extrusion granulator to attain the target size, dried by a fluidized-bed drier at the product temperature of 70° C. and screened to obtain a granular pesticide preparation containing 4 mass % of tricyclazole and 2 mass % of imidacloprid and having a diameter of 1.4 to 1.6 mm and a length of 3 to 9 mm. The granular pesticide preparation was put in a Petri dish containing water and observed, and as a result, the preparation was rapidly settled in after putting into water, particles of the preparation were disintegrated on the bottom of the Petri dish within 30 minutes, and the non-disintegrable pesticide granules contained in the preparation dispersed without disintegration.

Test Example 1

Test for Dissolution in Water

A 900 ml volume of degree 3 hard water was taken in a glass-made Petri dish of 15 cm diameter to give a water depth of 5 cm. Each of the granular pesticide preparations of Examples 1-6 and Comparative Examples 1-4 was applied thereto for treatment in an amount corresponding to 1 kg per 10 ares. The water was taken after 1, 3, 7, 21 and 35 days from the treatment and was analyzed by the HPLC analysis to determine the concentration of the ingredient as the rate of dissolution in water. The results are shown in Table 1.

TABLE 1

|  | Pesticidal active ingredient | 1 Day | 3 Days | 7 Days | 21 Days | 35 Days |
|---|---|---|---|---|---|---|
| Example 1 | Bensulfuron-methyl | 53 | 67 | 81 | 90 | 87 |
|  | Mefenacet | 21 | 42 | 72 | 86 | 90 |
| Example 2 | Compound A | 15 | 27 | 55 | 67 | 76 |
|  | Fentrazamide | 85 | 96 | 98 | 100 | 98 |
| Example 3 | Compound A | 21 | 32 | 45 | 59 | 68 |
|  | Pentoxazone | 16 | 19 | 29 | 30 | 34 |
| Example 4 | Compound A | 42 | 55 | 67 | 88 | 87 |
|  | Cafenstrole | 43 | 73 | 93 | 96 | 100 |
| Example 5 | Compound B | 12 | 19 | 38 | 70 | 89 |
|  | Pyriminobac-methyl | 84 | 86 | 90 | 91 | 93 |
|  | Pentoxazone | 24 | 30 | 42 | 41 | 48 |
| Example 6 | Tricyclazole | 47 | 52 | 60 | 79 | 85 |
|  | Imidacloprid | 93 | 100 | 100 | 98 | 100 |
| Comparative Example 1 | Bensulfuron-methyl | 95 | 95 | 100 | 94 | 90 |
|  | Mefenacet | 19 | 39 | 75 | 92 | 84 |
| Comparative Example 2 | Compound A | 100 | 100 | 98 | 100 | 96 |
|  | Fentrazamide | 49 | 65 | 82 | 100 | 96 |
| Comparative Example 3 | Compound B | 100 | 98 | 97 | 100 | 97 |
|  | Pyriminobac-methyl | 70 | 85 | 96 | 98 | 100 |
|  | Pentoxazone | 6 | 11 | 19 | 21 | 25 |
| Comparative Example 4 | Tricyclazole | 97 | 100 | 100 | 100 | 96 |
|  | Imidacloprid | 100 | 100 | 100 | 100 | 96 |

As is understood from Table 1, as to the granular pesticide preparations of Examples 1-5, the rates of in-water dissolution of the sulfonylurea-based compounds or the difluoromethanesulfonylanilide derivatives or the salts thereof as the herbicides for the pesticidal active ingredient were running low in the tests after 1 day through 35 days from the treatment as compared with Comparative Examples 1-3 to indicate sustained-releasability and that, also in Example 6 with tricyclazole which is a fungicide, sustained-releasability was attained in view of the rate of in-water dissolution as compared with Comparative Example 4.

In addition, as to the pesticide preparations of Examples 1, 2 and 6, although the acidic pesticidal active ingredient was sustained-release as compared with the pesticide preparations of Comparative Examples 1, 2 and 4, other pesticidal active ingredients are not influenced by the dissolution control mechanism and indicate the equivalent rate of the in-water dissolution.

It is also understood that, as to the pesticide preparation of Example 5, although the acidic pesticidal active ingredient is sustained-release as compared with the pesticide preparation of Comparative Example 3, the rate of in-water dissolution of other pesticidal active ingredients can be enhanced.

Test Example 2

Biological Effectiveness Test: Paddy Rice

A 100 cm$^2$ wide plastic pot was filled with a paddy field soil and, after watering and shuffling, seeds of each of early watergrass, heartshape false pickerelweed and HOTARU-I were sowed in a depth of 0.5 cm. Further, two paddy rice plants at the two-leaves stage were transplanted in a transplanting depth of 2 cm followed by pooling of water in a depth of 5 cm. On the seventh day after transplantation, the granular pesticide preparations obtained in Examples 1, 2 and 5 and Comparative Example 1 to 3 were evenly applied for treatment in an amount corresponding to 1 kg/10 ares by weighing. The plants on these plastic pots were grown in a greenhouse and, after 28 days from the treatment, evaluation was made by the following criteria for the herbicidal effects and the extent of chemical damages. The results are shown in Table 2.

Evaluation criteria for herbicidal effects (growth suppression) and chemical damages
5: 90% or higher
4: 70% or higher but lower than 90%
3: 50% or higher but lower than 70%
2: 30% or higher but lower than 50%
1: 10% or higher but lower than 30%
0: lower than 10%

TABLE 2

|  | Pesticidal effects | | | Chemical damages paddy rice |
| --- | --- | --- | --- | --- |
|  | early watergrass | heartshape false pickerel-weed | HOTARU-I |  |
| Example 1 | 5.0 | 4.5 | 5.0 | 0 |
| Example 2 | 5.0 | 5.0 | 5.0 | 0.5 |
| Example 5 | 5.0 | 4.5 | 5.0 | 0 |
| Comparative Example 1 | 3.5 | 4.5 | 4.5 | 0.5 |
| Comparative Example 2 | 3.5 | 4.5 | 4.5 | 1.5 |
| Comparative Example 3 | 4.0 | 4.0 | 5.0 | 1.0 |

It is understood from Table 2 that the granular pesticide preparations of the Examples exhibited excellent herbicidal effects almost without chemical damages to the paddy rice while those of Comparative Examples 1 to 3 exhibited chemical damages to the paddy rice and stable efficacy could not be obtained against early watergrass.

INDUSTRIAL UTILIZABILITY

The granular pesticide preparation of the present invention can be prepared by a simple and easy method and enables dissolution control respectively needed for each pesticidal active ingredient to be compounded, and thereby shows stable efficacy of pesticidal active ingredients for a long term as well as capable of exhibiting stable efficacy against objective pests and weeds with a decrease in or prevention of the chemical damages or, for example, the chemical damages against the target crops caused by the pesticidal active ingredient with a decreased load on the environments by not using more than required amount of a pesticidal active ingredient but optimizing.

The invention claimed is:

1. A granular pesticide composition enabling dissolution control for each pesticidal active ingredient, having a granule size of 0.3 to 3 mm in diameter or of 0.6 to 3 mm in breadth and 2 to 10 mm in length, which comprises a non-disintegrable part in the form of granules being not disintegrated in water within 30 minutes and a disintegrable part being disintegrated in water within 30 minutes,
   wherein the non-disintegrable part contains (a) first acidic pesticidal active ingredient selected from sulfonylurea-based compounds and difluoromethanesulfonylanilide compounds represented by the formula,

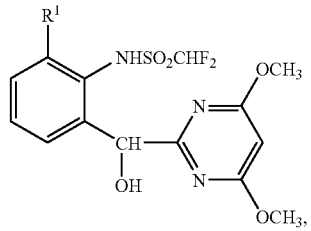

wherein $R^1$ is a hydrogen atom, alkyl group or alkoxyalkyl group, and salts thereof, (b) a cationic surfactant which is gelled in water selected from dialkyldimethylammonium chlorides wherein the alkyl part has 8-22 carbon atoms, and (c) a basic substance having a pH of 7.5 or higher in a 1 wt % aqueous solution or a 1 wt % aqueous suspension, and
   wherein the disintegrable part contains a second pesticidal active ingredient selected from compounds other than the first acidic pesticidal active ingredient (a).

2. The granular pesticide composition according to claim 1, wherein the basic substance is sodium hydrogen carbonate, sodium carbonate, calcium hydroxide, calcium carbonate, basic white carbon or basic Japanese acid clay.

3. The granular pesticide composition according to claim 1, wherein the cationic surfactant is dilaurydimethylammonium chloride, dioleyldimethylammonium chloride, dicocoyldimethylammonium chloride or distearyldimethylammonium chloride.

4. A process of preparing a granular pesticide composition enabling dissolution control for each pesticidal active ingredient according to claim 1, which process comprises the step of subjecting granules as the non-disintegrable part containing a first pesticidal active ingredient, a cationic surfactant and a basic substance, a second a pesticidal active ingredient, a nonionic or anionic surfactant and an extender to an extrusion granulation through a screen of which the mesh opening has a diameter larger than the granule size or granule length of the non-disintegrable part to form granules of the granular pesticidal composition enabling dissolution control for each pesticidal active ingredient having a granule size of 0.3 to 3 mm in diameter or of 0.6 to 3 mm in breadth and 2 to 10 mm in length, wherein the first acidic pesticidal active ingredient is selected from sulfonylurea-based compounds and difluoromethanesulfonylanilide derivatives represented by the formula,

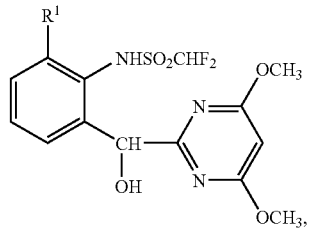

wherein $R^1$ is a hydrogen atom, alkyl group or alkoxyalkyl group, and salts thereof wherein the cationic surfactant which is gelled in water is selected from dialkyldimethylammonium chlorides wherein the alkyl part has 8-22 carbon atoms, wherein the basic substance has a pH of 7.5 or higher in a 1 wt. % aqueous solution or a 1 wt. % aqueous suspension, and
   wherein the second pesticidal active ingredient is selected from compounds other than the first acidic pesticidal active ingredient.

* * * * *